United States Patent [19]

Lindner et al.

[11] 4,276,426

[45] Jun. 30, 1981

[54] PROCESS FOR THE PREPARATION OF ORGANOSILICON COMPOUNDS

[75] Inventors: Tassilo Lindner, Mehring-Öd; Norbert Zeller, Burghausen; Volker Frey, Burghausen; Rudolf Riedle, Burghausen; Peter John, Burghausen, all of Fed. Rep. of Germany; Georg Engelsberger, Ach, Austria

[73] Assignee: Wacker-Chemie GmbH, Munich, Fed. Rep. of Germany

[21] Appl. No.: 98,005

[22] Filed: Nov. 28, 1979

[30] Foreign Application Priority Data

Nov. 28, 1978 [DE] Fed. Rep. of Germany ....... 2851456

[51] Int. Cl.$^3$ .............................. C07F 7/09; C07F 7/08
[52] U.S. Cl. .................................................... 556/479
[58] Field of Search ........................................ 556/479

[56] References Cited

U.S. PATENT DOCUMENTS

| 2,626,268 | 1/1953 | Barry et al. | 556/479 |
| 3,277,135 | 10/1966 | Harding et al. | 556/479 |
| 3,624,119 | 11/1971 | Stotzbach et al. | 556/479 |
| 3,793,358 | 2/1974 | Bauer et al. | 556/479 |

FOREIGN PATENT DOCUMENTS 116640 4/1958 U.S.S.R. .................................... 556/479

OTHER PUBLICATIONS

"J.A.C.S.", 82, p. 3603, Method B, 1960.

*Primary Examiner*—Paul F. Shaver

[57] ABSTRACT

This invention relates to the preparation of organosilicon compounds by the addition of a silicon compound containing Si-bonded hydrogen to a compound having an aliphatic multiple bond in the presence of a catalyst which promotes the addition of Si-bonded hydrogen to compounds containing an aliphatic multiple bond. In this process the reactants and the catalyst are continuously introduced into a pipe-shaped reactor while the contents of the reactor, which are maintained in a liquid phase by the application of pressure are circulated in the reactor at a rate of at least 1,000 cm per minute and while the reaction mixture is continuously being removed from the reactor.

7 Claims, No Drawings

PROCESS FOR THE PREPARATION OF ORGANOSILICON COMPOUNDS

The present invention relates to a process for preparing organosilicon compounds and more particularly to an improved process for preparing organosilicon compounds by the addition of a silicon compound having Si-bonded hydrogen to a compound containing an aliphatic multiple bond in the presence of a catalyst which promotes the addition of Si-bonded hydrogen to an aliphatic multiple bond.

BACKGROUND OF THE INVENTION

Processes for preparing organosilicon compounds by the addition of organosilicon compounds containing an aliphatic multiple bond in the presence of a catalyst which promotes the addition of Si-bonded hydrogen to an aliphatic multiple bond are known in the art. For example, J. W. Ryan, et al describe in the *Journal of the American Chemical Society*, Volume 82 (1960) Page 3603 (Method B), a process for preparing organosilicon compounds which comprises continuously adding a silicon compound having Si-bonded hydrogen and a compound having an aliphatic multiple bond and a catalyst which promotes the addition of the Si-bonded hydrogen to the aliphatic multiple bond into a pipe-shaped reactor while maintaining the contents of the reactor in a liquid phase and while continuously removing the reaction mixture from the reactor.

Compared to the processes known heretofore, the process of this invention has the advantage that the reactor can be run for a longer period of time without a shutdown when at least one of the reactants or reaction products have a tendency towards polymerization. Moreover, the process of this invention has the added advantage that fewer undesirable by-products are produced, which results in increased space/time yields.

It is therefore, an object of this invention to provide an improved process for preparing organosilicon compounds. Another object of this invention is to provide an improved process for preparing organosilicon compounds by the addition of silicon compounds having Si-bonded hydrogen to a compound having an aliphatic multiple bond in the presence of a catalyst which promotes the addition of Si-bonded hydrogen to an aliphatic multiple bond. A further object of this invention is to provide an improved process for preparing organosilicon compounds in which the reactor can be operated for a longer period of time even when one of the reactants or reaction products have a tendency towards polymerization. A still further object of this invention is to provide an improved process for preparing organosilicon compounds having fewer by-products.

SUMMARY OF INVENTION

The foregoing objects and others which will become apparent from the following description are accomplished in accordance with this invention, generally speaking, by providing an improved process for preparing organosilicon compounds by the continuous introduction of a silicon compound having Si-bonded hydrogen, a compound containing an aliphatic multiple bond and a catalyst which promotes the addition of Si-bonded hydrogen to an aliphatic multiple bond to a pipe-shaped reactor, where the reaction mixture is maintained in a liquid phase and is being continuously removed from the reactor, the improvement which comprises circulating the reaction mixture at a rate of at least 1,000 cm per minute in the reactor.

DETAILED DESCRIPTION OF THE INVENTION

All silicon compounds having Si-bonded hydrogen which have or could have been used heretofore in the known processes for the continuous preparation of organosilicon compounds by the addition of a silicon compound having Si-bonded hydrogen to a compound having an aliphatic multiple bond in the presence of a catalyst which promotes the addition in a pipe-shaped reactor may be used in the process of this invetion. Suitable silicon compounds are silanes of the general formula:

$$[R(O)_b]_a HSiX_{3-a},$$

in which R represents the same or different, monovalent hydrocarbon radicals or substituted monovalent hydrocarbon radicals free of aliphatic multiple bonds and having from 1 to 18 carbon atoms, X represents the same or different halogen atoms, a is 0, 1, 2 or 3 and b is 0 or 1. Other organosilicon compounds which may be used are those having the general formula:

$$X_{2-c}[R(O)_b]_c HSiR''SiH_{b'}[(O)_bR]_a X_{3-a-b'}$$

where R, X and b are the same as above, R'' is a bivalent hydrocarbon radical having from 2 to 18 carbon atoms, b' is 0 or 1, c is 0, 1 or 2 and the sum of a and b' is no more than 3; as well as disiloxanes of the general formula:

$$X_{2-c}[R(O)_b]_c HSiOSiH_{b'}[(O)_bR]_a X_{3-a-b'}$$

where X, R, a, b, b' and c are the same as above.

Examples of hydrocarbon radicals represented by R are alkyl radicals, such as the methyl, ethyl, n-propyl, isopropyl, n-butyl, sec-butyl, 2-ethylhexyl as well as octadecyl radicals; cycloalkyl radicals such as the cyclohexyl radical; and aryl radicals, such as the phenyl radical. Examples of substituted hydrocarbon radicals represented by R are halogenated hydrocarbon radicals, such as the 1,1,1-trifluoropropyl radical. An example of a hydrocarbon radical represented by R'' is the ethylene radical.

It is preferred that the halogen atom represented by X be chlorine; however, X may represent other halogen atoms such as fluorine, bromine or iodine. Suitable examples of silicon compounds having Si-bonded hydrogen which may be employed in the process of this invention are trichlorosilane, methyldichlorosilane, trimethylsilane, methylphenylchlorosilane, dimethylchlorosilane, trimethoxysilane; organosilicon compounds of the formula:

$$Cl_2HSiCH_2CH_2SiHCl_2$$

and disiloxanes of the formula:

$$H(CH_3)_2SiOSi(CH_3)_2H.$$

Compounds having an aliphatic multiple bond which have or could have been used heretofore in processes for the continuous preparation of organosilicon compounds by the addition of a silicon compound having Si-bonded hydrogen to a compound having an aliphatic multiple bond in a pipe-shaped reactor in the presence of a catalyst which promotes the addition of silicon bonded hydrogen to aliphatic multiple bonds, may be used in the process of this invention.

Suitable examples of compounds having an aliphatic multiple bond which may be used in the process of this invention are acetylene, ethylene, propylene, various pentenes, such as n-pentene-1, and 2,4,4-trimethylpentene-1, 1-methylstyrene, styrene, vinylcyclohexene-3, allyl chloride, allyl methacrylate, vinyl chloride and 1,1,1-trifluoropropylene-(3) as well as allyl succinic acid di-n-butyl ester.

Although it is preferred that the silicon compound having Si-bonded hydrogen and the compound containing an aliphatic multiple bond be used in equimolar quantities, one of these compounds may be used in excess.

Any catalyst which has been used heretofore to promote the addition of a silicon compound contain Si-bonded hydrogen to a compound having an aliphatic multiple bond, in a process in which the reactants and the catalyst are continuously introduced into a pipe-shaped reactor while continuously removing the reactants from the reactor, may be used in the process of this invention. Examples of suitable catalysts are the so-called hydrosilation catalysts which may be used in a homogeneous phase. Examples of such hydrosilation catalysts are compounds or complexes of Pt, Rh, Pd, Co, Ni and Fe, such as $H_2PtCl_6.6H_2O$, platinum-olefin complexes, platinum-alcohol complexes, platinum-alcoholate complexes, platinum-ether complexes, platinum-aldehyde complexes, platinum-ketone complexes, e.g., the reaction product of $H_2PtCl_6.6H_2O$ and cyclohexanone, platinum-vinylsiloxane complexes, especially platinum-divinyltetramethyldisiloxane complexes which are free of or contain a detectable amount of halogen, bis-(gamma-picoline)-platinum dichloride, trimethylene-dipyridine-platinum dichloride, as well as iron, nickel and cobalt carbonyls.

Promotors, such as phenothiazine, diphenylamine, N,N-diphenyl-p-phenylenediamine and/or phenoxazine (cf. U.S. Pat. No. 3,925,434, to V. T. Chuang) may be co-employed. The term "catalyst" as used herein also includes the use of such promoters.

In the process of this invention, the amount of catalyst used to promote the addition of a silicon compound having Si-bonded hydrogen to a compound containing an aliphatic multiple bond, may be the same amount as used heretofore in the known processes for the preparation of organosilicon compounds by the addition of a silicon compound having Si-bonded hydrogen to a compound having an aliphatic multiple bond in the presence of a catalyst which promotes the addition of a silicon compound having Si-bonded hydrogen to a compound having an aliphatic multiple bond in a batch or continuous process. Generally, the amount of catalyst which is used to promote the addition of a silicon compound having Si-bonded hydrogen to a compound containing an aliphatic multiple bond is in the range of from about $10^{-7}$ to $10^{-3}$ mol per gram atom of Si-bonded hydrogen present on the silicon compound having Si-bonded hydrogen.

The reactants and the catalyst may be introduced continuously, but separately into the pipe-shaped reactor, or they may be mixed and introduced continuously. Preferably, the reactants and the catalyst are introduced separately, but continuously into the pipe-shaped reactor.

In the process of this invention, it is preferred that there be a distance of at least 5 meters between the point where the reactants and the catalyst are introduced into the pipe-shaped reactor and the point where the reaction mixture is removed from the reactor. There is no upper limit as to the length of the pipe reactor. Thus, the pipe-shaped reactor could for example be 20 meters long. It is preferred that the inside diameter of the pipe-shaped reactor be uniform throughout its length, preferably from 5 to 20 mm in diameter.

The use of pressure to maintain the reaction mixture in the liquid phase is required when one of the reactants or the reaction products would form a gaseous phase in the reactor in the absence of pressure. When, for example at least one of the reactants and/or reaction products boils at the temperature employed when the pressure is only 1 bar, then it is essential that sufficient pressure be used to maintain the contents of the reactor in the liquid phase. A pressure of 6 bar is generally sufficient; however, higher or lower pressures may be used as well.

There is no upper limit in regard to the speed with which the contents of the reactor may be circulated in the reactor. Thus, the contents of the reactor may be circulated in the reactor at a speed of for example 7,000 cm per minute.

The catalyst activity, amount of catalyst, the length of time the reaction mixture remains in the reactor, and the temperature are preferably selected so that at least 90 mol percent of the silicon compound having Si-bonded hydrogen is reacted before the reaction mixture leaves the reactor.

In order to ensure that at least 90 mol percent of the silicon compound having Si-bonded hydrogen is reacted before the reaction mixture leaves the reactor, it is preferred that the reaction mixture remain in the reactor for from 5 to 12 minutes and that the temperature of the reactor be from about 90° to about 190° C.

The catalyst solution used in the following examples, including the comparison examples, was obtained by heating for 1 hour a solution containing 2.12 g of $H_2PtCl_6.6H_2O$ in 200 ml of cyclohexanone to a temperature of 100° C., and thereafter the solution thus obtained was dried with the aid of anhydrous sodium sulfate.

EXAMPLE 1

A U-shaped, steel pipe 10 meters long having an inside diameter of 9 mm is used as a reactor. The reactor is provided on one end with a means for addition of the reactants and the catalyst and at the other end the reactor is provided with a means for removing the reaction mixture. A short distance downstream from the point of addition of the reactants and the catalyst and a short distance downstream from the point where the reaction mixture is removed, is a conduit which has a diameter of 9 mm and connects the two ends of the reactor in order to make it possible to circulate the reaction mixture with the aid of a circulating pump. The reactor is first filled with a mixture containing 1.3 liters of trichlorosilane and 1.7 liters of allyl methacrylate. The mixture is circulated in the reactor by the pump at the rate of 3,500 cm per minute and heated by means of an oil bath which is traversed by a section of the reactor. As soon as the temperature reaches 140° C., 1.3 liters of trichlorosilane, 1.7 liters of allyl methacrylate and 2.5 ml of the catalyst solution are added per hour into the reactor whose contents continue to be circulated at the rate of 3,500 cm per minute, while the contents of the reactor are kept at a temperature of 140° C. and the pressure in the reactor is maintained at 6 bar with the aid of pressure maintenance valves located between the point where the reaction mixture leaves the reactor and a condenser for the reaction mixture which is continuously being removed from the reactor. About 98 mol percent of the trichlorosilane is reacted and 12.5 mol of methacryloxypropyltrichlorosilane per hour is obtained. Gas chromatography indicates that the product's purity is 96.4 percent by weight.

Comparison Example A

The process described in Example 1 is repeated, except that the contents of the reactor are not circulated. After 1 hour the contents of the reactor jelled and the reaction is terminated.

EXAMPLE 2

The reactor described in Example 1 is filled with a mixture containing 1.8 liters of trichlorosilane and 1.2 liters of allyl chloride and the contents are circulated in the reactor with the aid of a pump at the rate of 3,500 cm per minute while being heated with an oil bath. As soon as the temperature reaches 120° C., 1.8 liters of trichlorosilane, 1.2 liters of allyl chloride and 10 ml of the catalyst solution are introduced per hour into the reactor while the contents of the reactor continue to be circulated at the rate of 3,500 cm per minute at a temperature of 120° C., and at a pressure of 6 bar with the aid of a pressure maintenance valve located between the outlet point on the reactor and the condenser for the withdrawn reaction mixture which is continuously being removed from the reactor. About 99.6 percent of the trichlorosilane is converted and 3.5 kg per hour of the reaction mixture is obtained. The reaction mixture contains the following silicon compounds:

|  | Parts by weight |
|---|---|
| HSiCl$_3$ | 1 |
| SiCl$_4$ | 58 |
| CH$_3$(CH$_2$)$_2$SiCl$_3$ | 62 |
| Cl(CH$_2$)$_3$SiCl$_3$ | 223 |

EXAMPLE 3

The procedure described in Example 2 is repeated, except that 1.9 liters of methyldichlorosilane, 1.1 liters of allyl chloride and 10 ml of the catalytic solution are substituted for the trichlorosilane, allyl chloride and the catalytic solution and the process is carried out at 170° C. instead of 120° C. About 99.1 mol percent of the methydichlorosilane is reacted and about 3.1 kg per hour of material is obtained which contains the following silicon compounds.

|  | percent by weight | For comparison purposes, the composition of the product obtain from the cited literature*: percent by weight |
|---|---|---|
| Propene | 0.9 | 4.9 |
| (CH$_3$)HSiCl$_2$ | 0.6 | 14.7 |
| ClCH$_2$CH=CH$_2$ | 0.7 | 5.3 |
| CH$_3$SiCl$_3$ | 20.3 | 21.0 |
| CH$_3$(CH$_2$)$_2$Si(CH$_3$)Cl$_2$ | 21.3 | 12.6 |
| Cl(CH$_2$)$_3$Si(CH$_3$)Cl$_2$ | 54.2 | 41.5 |

*Journal of the American Chemical Society Vol. 82(1960), page 3603 (Method B)

This corresponds to a space/time yield of 2.64 kg/liter/hour of chloropropylmethyldichlorosilane when the process of this invention is used.

Comparison Example B

The process described in Example 3 is repeated, except that the reactor's contents are not circulated. The space/time yield in chloropropylmethyldichlorosilane is only 1.63 kg/liter/hour.

EXAMPLE 4

The process described in Example 2 is repeated, except that 1.5 liters of a mixture prepared from isomeric pentenes (10 percent by weight of 2-methylbutene-1, 82 percent by weight of 2-methylbutene-2 and 8 percent by weight of pentenes having an undetermined structure) and 10 ml of the catalytic solution are substituted for the trichlorosilane, allyl chloride and catalytic solution. About 98.6 percent of the trichlorosilane employed is reacted and 14.5 mol percent per hour of pentyltrichlorosilane is obtained. The product's purity is 92.5 percent by weight as determined by gas chromatography.

EXAMPLE 5

The process described in Example 2 is repeated, except that 1.2 liters of trichlorosilane, 1.8 liters of diisobutylene (a mixture of 2,4,4-trimethylpentene-1 and 2,4,4-trimethylpentene-2) and 10 ml of the catalytic solution are substituted for the trichlorosilane, allyl chloride and catalytic solution. About 98.6 mol percent of the trichlorosilane employed is reacted and 11.6 moles per hour of 2,4,4-trimethylpentyltrichlorosilane are obtained.

EXAMPLE 6

The process described in Example 2 is repeated, except that 1.3 liters of methyldichlorosilane, 1.7 liters of 1-methylstyrene and 5 ml of the catalytic solution are substituted for the trichlorosilane, allyl chloride and catalytic solution and the process is carried out at a temperature of 140° C. instead of 120° C. About 97.9 mol percent of the methyldichlorosilane used is converted and 12.8 moles per hour of 2-phenyl-2-methylethyl (methyl) dichlorosilane are obtained having a purity of 97.2 percent by weight as determined by gas chromatography.

EXAMPLE 7

The process described in Example 2 is repeated, except that 1.3 liters of trichlorosilane, 1.7 liters of vinylcyclohexanone-3 and 5 ml of the catalytic solution are substituted for the trichlorosilane, allyl chloride and catalytic solution and the process is carried out at 140° C. instead of 120° C. About 99.6 mol percent of the trichlorosilane is reacted and each hour 12.7 mole of 2-cyclohexene-3-yl-ethyltrichlorosilane is obtained. The purity is about 98.7 percent by weight as determined by gas chromatography.

What is claimed is:

1. An improved process for preparing organosilicon compounds by the continuous introduction into a pipe-shaped reactor a compound having Si-bonded hydrogen, a compound containing an aliphatic multiple bond and a catalyst which promotes the addition of Si-bonded hydrogen to an aliphatic multiple bond, in which the reaction mixture is maintained in a liquid phase by the application of pressure, while the reaction mixture is being continuously removed from said reactor, the improvement which comprises continuously circulating the reaction mixture in the reactor at a rate of at least 1,000 cm per minute.

2. The improved process of claim 1, wherein, the reaction mixture is retained in the reactor until at least 90 mol percent of the amount of silicon compound containing Si-bonded hydrogen is reacted before being removed from the reactor.

3. The improved process of claim 1 or 2, wherein the reaction mixture remains in the reactor from 5 to 12 minutes while the temperature inside the reactor is from 90° to 190° C.

4. The improved process of claim 1, 2 or 3, wherein the length of the reactor is from 5 to 20 meters and the inside diameter of the reactor is from 5 to 20 mm.

5. The improved process of claim 1, wherein the catalyst is present in an amount of from $10^{-7}$ to $10^{-3}$ mol per gram atom of Si-bonded hydrogen on the silicon compound containing Si-bonded hydrogen.

6. The improved process of claim 1, wherein the organosilicon compound having Si-bonded hydrogen, the compound containing an aliphatic multiple bond and the catalyst are mixed just prior to their addition to the pipe-shaped reactor.

7. The improved process of claim 1, wherein the organosilicon compound having Si-bonded hydrogen, the compound containing an aliphatic multiple bond and catalyst are each added separately but continuously to the pipe-shaped reactor.

* * * * *